United States Patent [19]

Aida et al.

[11] 4,415,508
[45] Nov. 15, 1983

[54] APPARATUS FOR MIXING GASES

[75] Inventors: Kenji Aida, Yokosuka; Takeshi Yamamoto, Tokyo; Toshihiko Kumazawa, Yokohama, all of Japan

[73] Assignee: Nippon Shokubai Kagaku Kogyo Co., Ltd., Japan

[21] Appl. No.: 196,935

[22] Filed: Oct. 14, 1980

Related U.S. Application Data

[62] Division of Ser. No. 953,568, Oct. 23, 1978, Pat. No. 4,256,604.

Foreign Application Priority Data

[30]

Oct. 26, 1977 [JP] Japan .............................. 52-127646

[51] Int. Cl.$^3$ .............................................. B01F 3/04
[52] U.S. Cl. .......................... 261/114 R; 261/114 A; 261/124; 55/255; 55/259
[58] Field of Search ............... 261/114 R, 124, 114 A; 55/259, 255

[56]  References Cited

U.S. PATENT DOCUMENTS

| | | | |
|---|---|---|---|
| 1,748,411 | 2/1930 | Cooke | 55/255 |
| 2,234,057 | 3/1941 | Mount | 261/114 R |
| 2,707,163 | 4/1955 | Thibaut | 261/114 A |
| 2,762,692 | 9/1956 | Spitz et al. | 261/114 R |
| 2,853,281 | 9/1958 | Hibshman et al. | 261/114 R |
| 3,094,574 | 6/1963 | Glasgow et al. | 261/114 R |
| 3,364,124 | 1/1968 | Walker et al. | 261/114 R |
| 3,545,411 | 12/1970 | Vollradt | 261/114 R |
| 3,975,164 | 8/1976 | Brown, Jr. | 261/114 R |

Primary Examiner—Tim R. Miles
Attorney, Agent, or Firm—Behr & Adams

[57]  ABSTRACT

An apparatus for mixing a hydrocarbon-containing gas flow with a molecular oxygen-containing gas flow, wherein at least one aqueous medium sealing zone allowing the hydrocarbon-containing gas flow to pass therethrough is provided by sealing a side of said introduced gas flow with an aqueous medium, providing at least one shielding zone for flame propagation, said gas flow is allowed to pass therethrough on a discharge side of said gas flow, and providing means for introducing the molecular oxygen-containing gas flow into a gas mixing zone defined between both of the above zones there to be thoroughly mixed with the hydrocarbon-containing gas flow.

12 Claims, 14 Drawing Figures

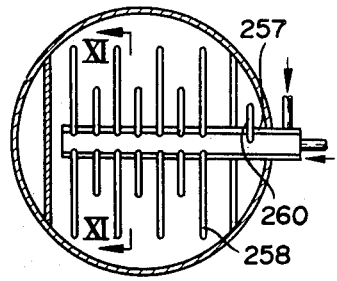
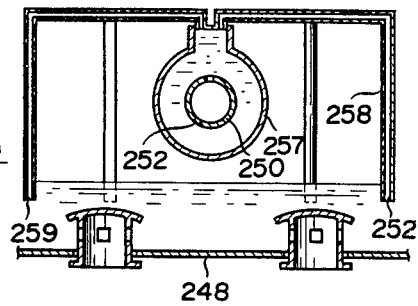
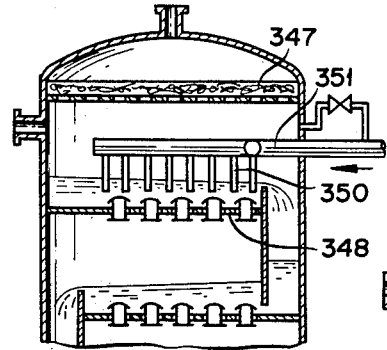
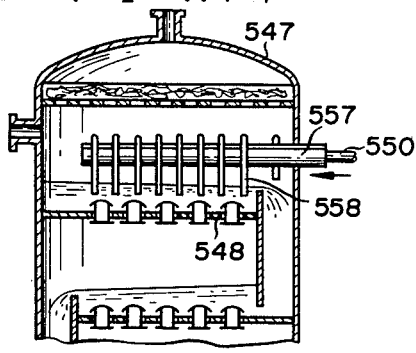
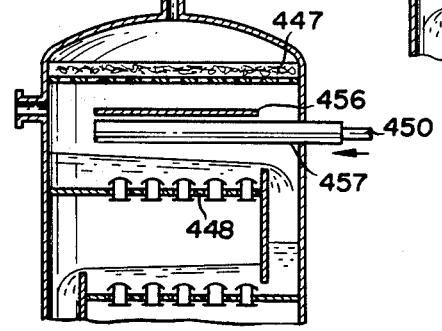

APPARATUS FOR MIXING GASES

This is a division of application Ser. No. 953,568, filed Oct. 23, 1978 now U.S. Pat. No. 4,256,604.

This invention relates to a method for mixing a hydrocarbon-containing gas flow with a molecular oxygen-containing gas flow and an apparatus used therefor. More specifically, it relates to, in processes for a catalytic gas phase oxidation of hydrocarbons such as ethylene, propylene, benzene, ortho-xylene, naphthalene and the like, in particular, for the process of producing ethylene oxide from ethylene through catalytic gas phase oxidation using molecular oxygen, a method for mixing thoroughly an ethylene-containing gas flow and a molecular oxygen-containing gas flow, as well as an apparatus used therefor.

In a catalytic gas phase oxidation of a hydrocarbon, for example, in the process of producing ethylene oxide from ethylene through its catalytic gas phase oxidation using molecular oxygen in the presence of a silver catalyst, a hydrocarbon-containing gas which contains saturated hydrocarbons such as methane, ethane and the like, nitrogen, carbon dioxide, argon, oxygen and the like in addition to ethylene are mixed with a molecular oxygen-containing gas comprising air, oxygen-enriched air or pure oxygen at a predetermined ratio and, thereafter, introduced into a reaction zone filled with the silver catalyst, and then the catalytic gas phase oxidation is conducted in the reaction zone. The gaseous reaction products containing ethylene oxide thus produced in the reaction zone are introduced to the bottom of an ethylene oxide absorption column and then contacted with an aqueous medium such as an aqueous solution of ethylene glycol introduced from the top of the above absorption column in a counter current whereby the ethylene oxide in the gas is separated by absorption. The solution containing ethylene oxide in the absorption column is discharged from its bottom to a ethylene oxide stripping column, where the ethylene oxide is separated, and the separated ethylene oxide is further sent to a purification step. Unabsorbed gases in the ethylene oxide absorption column are introduced, if necessary, to a carbon dioxide absorption column and, after the absorption of carbon dioxide into an aqueous alkali solution, re-conditioned into a starting material gas of a desired composition with a supply of ethylene and molecular oxygen, and then recycled to the reaction zone.

It is desired that the gas mixture to be circulated is out of the inflammability limit in any parts of the recycling process such as the reactor, the ethylene oxide absorption column and the carbon dioxide absorption column in the process for preparing ethylene oxide. Sometimes, gas mixture of a composition within the inflammability limit is, however, formed locally upon mixing the hydrocarbon-containing gas flow and the molecular oxygen-containing gas flow owing to insufficient mixing and back flow. In view of the above, various improvements have been proposed so as to mix as much as rapidly the hydrocarbon-containing gas flow with the molecular oxygen-containing gas flow to thereby decrease the insufficient gas mixture zone, or to prevent the back flow of the hydrocarbon-containing gas flow to a moelcular oxygen-containing gas conduit. In U.S. Pat. Nos. 3,706,534 and 3,702,619, for example, the above danger is reduced by dispersing the molecular oxygen-containing gas flow into the hydrocarbon-containing gas flow to mix them using a mixing apparatus comprising a ring with a plurality of tubes or orifices, or by adding a great amount of nitrogen into the molecular oxygen containing gas flow so as to prevent the back flow of the hydrocarbon-containing gas flow into a conduit of the molecular oxygen-containing gas flow. In these apparatus, however, interruption or re-starting of the apparatus occurs either intentionally or unintentionally due to periodical maintenance, failures, and stoppage of power supply and, in these unstationaly states, an energy sufficient to cause ignition is often produced locally leading to accidents such as destruction in the apparatus. In addition, the explosive danger is further amplified by the flame propagation caused by the local generation and accumulation of the ignition energy due to unexpected causes. It has, however, been very difficult to eliminate such danger in the conventional apparatus. Accordingly, no satisfactory methods for eliminating the ignition energy upon mixing the hydrocarbon-containing gas flow with the molecular oxygen-containing gas flow have not yet been attained and a considerable amount of nitrogen has to be used for the prevention of the back flow in the prior art.

Accordingly, it is an object of the present invention to provide a novel method for mixing a hydrocarbon-containing gas flow with a molecular oxygen-containing gas flow, as well as an apparatus used therefor.

It is another object of the present invention to provide a safety method for mixing the hydrocarbon-containing gas flow with the molecular oxygen-containing gas flow capable of reducing the amount of nitrogen used to zero or a sufficiently slight amount and eliminating the ignition energy, as well as an apparatus used therefor.

It is a further object of the present invention to provide a safety method for mixing the molecular oxygen-containing gas in a catalystic gas phase oxidation process of a hydrocarbon, as well as an apparatus used therefor.

The foregoing various objects can be attained by a method for mixing a hydrocarbon-containing gas flow with a molecular oxygen-containing gas flow, wherein at least one aqueous medium sealing zone allowing the hydrocarbon-containing gas flow to pass therethrough is provided by sealing a side of introducing the hydrocarbon-containing gas flow with an aqueous medium, and at least one shielding zone for flame propagation allowing the above gas flow to pass therethrough is provided on a side of discharging the gas flow, and the molecular oxygen-containing gas flow is introduced into a gas mixing zone defined between both of the above zones to be thoroughly mixed with the hydrocarbon-containing gas flow.

In other word, the foregoing objects can be attained in an appartus for mixing a hydrocarbon-containing gas flow with a molecular oxygen-containing gas flow comprising a cylindrical main body, a discharging exit and an introducing inlet for the hydrocrabon-containing gas flow provided respectively to the upper and the lower portions of the cylindrical main body, an introducing inlet and a discharging exit for an aqueous medium respectively provided to the upper and the lower portions of the cylindrical main body, at least one residence means for the aqueous medium provided on a side of introducing the gas flow in the main body and allowing the gas flow to pass therethrough in contaction with the aqueous medium and at least one shielding means for flame propagation provided on a side of discharging the hydrocarbon-containing gas flow in the main body and allowing the gas flow to pass therethrough and an introducing means for the molecular oxygen-containing gas flow disposed in a gas mixing chamber defined between the residence means and the shielding means.

In the gas mixing process according to the present invention, the hydrocarbon-containing gas is contacted with the aqueous medium in a counter current in a gas absorption column or a vessel equipped with a residence means for the aqueous medium such as trays or packings. While on the other hand, the molecular oxygen-containing gas is contacted with the aqueous medium in the aqueous medium residence zone or water and then introduced into a gas mixing zone, where it is mixed with the hydrocarbon-containing gas. The hydrocarbon-containing gas flow thoroughly mixed with the molecular oxygen-containing gas is sent, with or without passing through a further aqueous medium residence zone, passing through a demister provided on the uppermost stage of the mixing apparatus to a reaction process.

The gas mixing apparatus according to the present invention comprises in its inside at least one residence means for aqueous medium and a shielding means for flame propagation such as the above residence means for aqueous medium or the demister at its uppermost portion and it is substantially in the same structure as that of a gas absorption column. Accordingly, the above means for aqueous medium is usually composed of bubble cap trays, uniflax trays, sieve trays, ballast trays, valve trays, venturi trays, turbo-grid trays, dual float trays, kittel trays and the like. Layers of packings such as Rasching rings, Lessing rings, berl saddles, inter-lock saddles and the like can also be used. The above shielding means for flame propagation may be residence means for aqueous medium such as the above trays or packed layers, or a demister. Any types of demisters can be used so long as they have a mist separating function, with a wire mesh type demister being particularly suited. For the above residence means for aqueous medium, trays, among all, cross flow contaction type trays with a downcomer are most preferred. Accordingly, an absorption column of a conventional tray tower type or a packed column type is usually used for the mixing apparatus and a tray tower having a plurality of trays is preferred. However, those other than the absorption column but having the above structure can also be employed as the mixing apparatus.

An inlet for the hydrocarbon-containing gas and an exit for the aqueous medium are provided below the residence means for aqueous medium in the mixing apparatus and an exit for the gas mixture of the hydrocarbon-containing gas flow (a gaseous mixture of the hydrocarbon-containing gas flow and the molecular oxygen-containing gas flow) is provided above the shielding means for flame propagation. The inlet for the aqueous medium is provided above the shielding means for flame propagation if it comprises a residence means for aqueous medium and below the above shielding means if it comprises a demister.

A molecular oxygen-containing gas introducing means as detailed later is provided to a gas mixture chamber defined between the residence means for aqueous medium and the shielding means for flame propagation. Accordingly, the hydrocarbon-containing gas introduced through the inlet at the lower portion of the mixing apparatus rises passing through the aqueous medium layer on the tray in which the aqueous medium introduced from the upper inlet is resident and, after arriving at the gas mixing zone, mixed with the molecular oxygen introduced through the aqueous medium into this mixing zone. Then, the mixture is discharged through the shielding means for flame propagation such as a tray or a demister from an exit out of the mixing apparatus. While on the other hand, the aqueous medium to be supplied to the mixing apparatus is fed through the inlet from above the uppermost tray in the mixing apparatus, flows down passing through the lower trays successively and finally is discharged through the exit. Where a gas absorption column is used as the mixing apparatus, a desired component is dissolved, at the same time, into the aqueous medium and then removed out of the system from the bottom of the gas absorption column. The ratio between the flow rate of the aqueous medium and the hydrocarbon-containing gas may be such one that the upgoing gas does not blow out but stays as a liquid layer in the residence means for aqueous medium so as to conduct a sufficient gas-liquid contaction and the ratio can be determined using a calculation equation used for the design of absorption columns known to those skilled in the art. Accordingly, if the gas mixing apparatus also serves as a gas absorption column, the liquid-gas ratio (L/G) is increased.

The aqueous medium usable in the present invention is fresh water such as purified water and deionized water, or a recycling aqueous solution of absorbing water discharged from the bottom of the absorption column after recovered with predetermined components through separation, or a recycled aqueous solution containing components still remained unseparated after the recovery of specific components through separation or other components. The latter example includes, for example, an aqueous solution containing 0.1–30% by weight, in particular, 1–20% by weight of ethylene glycol used for the recovery of oxidation products of ethylene through absorption at the production of ethylene oxide.

The molecular oxygen-containing gas usable here includes, in addition to pure oxygen, pure oxygen diluted with an inert gas, oxygen-enriched air or air. The hydrocarbon-containing gas includes, for example, ethylene, propylene, isobutylene, benzene, ortho-xylene, naphthalene, as well as those gases produced by the catalytic gas phase oxidation of these hydrocarbons with the above molecular oxygen-containing gas and still containing unreacted hydrocarbons. Particularly, where the gaseous products from the catalytic gas phase oxidation containing unreacted hydrocarbons are used, the recovery of aimed products by absorption and the mixing with the molecular oxygen-containing gas can be conducted simultaneously.

Accordingly, the method of mixing and the apparatus used therefor according to the present invention can be suitably used in the process for producing ethylene oxide from ethylene, acrolein and acrylic acid or acrilonitrile from propylene, maleic anhydride from benzene, phthalic anhydride from naphthalene, napthoquinone from naphthalene and the like by catalytic gas phase oxidation using the molecular oxygen-containing gas. Particularly, this invention provides an excellent result in the process of producing ethylene oxide from ethylene by gas phase oxidation using pure oxygen.

In the method of mixing gas according to the present invention, a typical method for introducing the molecular oxygen-containing gas into the gas mixing zone includes the followings.

In a first type of the method for introducing the molecular oxygen-containing gas, a plurality of branched bundle of pipes each having one or more orifices at an end are provided to the gas mixing zone defined between the two residence means or aqueous medium, for example, between one tray and other tray. The ends of the bundle of pipes are uniformly arranged spaced apart from each other on the tray so as not to hinder the operation of the tray and the orifices are immersed in the aqueous medium layer residence on the tray in a depth of 1–10 cm. While the orifices are disposed so that they situate on a same level tray, about 0.1–3 cm differences is resulted in the height for the entire residence area. Then, if the amount of the molecular oxygen-containing gas is small, it only flows through some of the orifices and the aqueous medium may be back flown through the remaining orifices into the branched pipes. In order to avoid this, a slight amount of an inert gas such as nitrogen is added to the molecular oxygen-containing gas to overcome the above pressure difference of 0.1–3 cm in the column of the above aqueous medium, so that the molecular oxygen-containing gas may flow through all of the orifices in any flow rate. The molecular oxygen-containing gas blown out through the orifices at the end of the branched pipes into the aqueous medium is then contacted and mixed with the hydrocarbon-containing gas in the aqueous medium and then in the gas mixing zone.

In the second type of the method for introducing the molecular oxygen-containing gas, a double pipe composed of an inner pipe having a plurality of orifices and an outer pipe having an opening at its upper portion is inserted substantially horizontally into a gaseous portion in the gas mixing zone defined between two residence means for aqueous medium, for example, between adjacent trays. The molecular oxygen-containing gas is introduced into the inner pipe and water is introduced in the outer pipe continuously. The molecular oxygen-containing gas is dispersed through the orifice disposed in the lower portion of the inner pipe into the water layer in the outer pipe as gas bubbles and then released together with water through the opening in the upper portion of the outer pipe into the gas mixing zone and then mixed with the hydrocarbon-containing gas. The amount of water used may be such as equal to or more than the sum of the amount saturated in the molecular oxygen-containing gas and the amount entrained in splash. Since excess use of water only increases the cost, it is preferred to use water in an amount of 5–100 l/m³ gas volume in the state used. It is desired to use purified water or deionized water not substantially containing organics or halogens in order to avoid the contamination with organics caused by the back flow into the molecular oxygen-containing gas conduit pipe.

In the third type of the method for introducing the molecular oxygen-containing gas, which is the combined type of the above first and the second types, a double pipe composed of an inner pipe having a plurality of orifices and an outer pipe having a plurality of upwardly communicating branched bundle of pipes each with one or more orifices at an end is inserted in the gas mixing zone defined between the two residence means for aqueous medium, for example, beteen one tray and the other tray. The ends of the bundle of pipes are uniformly arranged spaced apart from each other on the tray as in the first type so as not to hinder the operation of the tray and immersed in the aqueous medium resident on the tray. The molecular oxygen-containing gas is introduced into the inner pipe and water is introduced in the outer pipe continuously. The molecular oxygen-containing gas is dispersed from orifice provided in the lower portion of the inner pipe into the water layer in the outer pipe as gas bubbles and then blown out together with the water discharged from the outer pipe by way of branched pipes connected to the upper portion of the outer pipe into the aqueous medium on the tray. Then, it is contacted and mixed with the hydrocarbon-containing gas at first in this aqueous medium and then in the gas mixing zone. The amount and the quality of water supplied to the outer pipe are the same as in the second type and the immersion depth and the arrangement of the orifices are the same as those in the first type.

The fourth type of the method for introducing the molecular oxygen-containing gas is the same as the method of the above first type excepting that the introducing means for molecular oxygen-containing gas is provided in the gas mixing zone defined between the aqueous medium residence means, for example, between a tray and a demister.

The fifth type of the method for introducing the molecular oxygen-containing gas is the same as the method of the above second type excepting that the introducing means for the molecular oxygen-containing gas is provided to the gas mixing zone defined betwen the residence zone for aqueous medium, for example, between a tray and a demister.

The sixth type of the method for introducing the molecular oxygen-containing gas is the same as the method of the above third type excepting that the introducing means for the molecular oxygen-containing gas is provided to the gas mixing zone defined between the residence zone for aqueous medium, for example, between a tray and a demister.

According to this invention, since the gas mixing zone is formed by sealing the side of introducing the hydrocarbon-containing gas with the aqueous medium on the residence means for aqueous medium and sealing the side of discharging the hydrocarbon-containing gas (gaseous mixture with molecular oxygen-containing gas) with the aqueous medium on the residence means for aqueous medium or shielding with the demister, if an ignition energy should be generated by some causes, the energy is absorbed by these sealing or shielding means and, if combustion should be taken place in a local region liable to enter the inflammability limit, the time can be shielded in the above sealing zone thereby inhibiting the flame from propagating out of the gas mixing zone. In addition, since the molecular oxygen introduced into the gas mixing zone is mixed with the hydrocarbon-containing gas after the contaction with the aqueous medium or water, if the pressure on the side of the molecular oxygen-containing gas should be lowered, there is no danger that the gas on the side of the molecular oxygen-containing gas should enter the inflammability limit owing to the presence of water. Further more, in each of the second, third, fourth fifth and sixth types of introducing method, no additional incorporation of the inert gas such as nitrogen is necessary even when the flow rate of the molecular oxygen-containing gas is low. In the introducing method of the first and the fourth type, it is also sufficient to add a slight amount of an inert gas enough to compensate the difference in the immersed thickness of the orifices.

The present invention will be understood best in connection with the accompanying drawings wherein:

FIG. 10 is a cross sectional view taken along line X—X in FIG. 9;

FIG. 11 is an enlarged cross sectional view of a part taken along line XI—XI in FIG. 10;

FIG. 12 is a vertical cross sectional view for a part showing a still further embodiment of the mixing apparatus according to the present invention;

FIG. 13 is a vertical cross sectional view of a still further embodiment of the mixing apparatus according to the present invention; and FIG. 14 is a vertical cross sectional view of a part showing a still further embodiment of the mixing apparatus according to this invention.

The process of mixing gas and the apparatus used therefor according to the present invention will be described by way of examples applied to the process for the production of ethylene oxide referring to the accompanying drawings.

Figure 1:
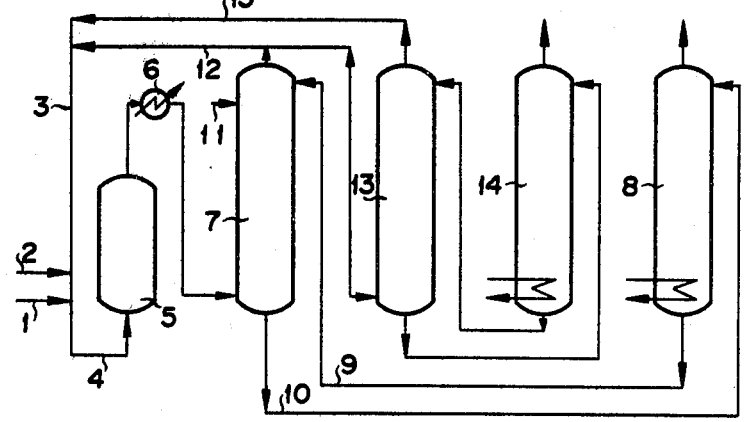
FIG. 1 is a flow sheet showing one example, wherein the method for mixing molecular oxygen gas is applied to a process for producing ethylene oxide by oxidation reaction using oxygen.

FIG. 1 is a flow sheet showing the principle of an oxidation process using oxygen, in which ethylene supplied from a line 1 and a dilution gas such as methane and ethane supplied from a line 2 are mixed with a gaseous mixture containing ethylene and oxygen recycled from a line 3 and then fed through a line 4 into a reactor 5, where the catalystic gas phase oxidation is conducted. The ethylene oxide-containing gaseous reaction products leaving the reactor 5 are cooled to a predetermined temperature in a cooler 6, introduced into the lower portion of an ethylene oxide absorption column 7 at a pressure of 2–40 kg/cm² where they are contacted with water at a temperature of at most 40° C. introduced from the top of the column 7 or with an absorbing solution comprising an aqueous solution of ethylene glycol at a temperature of at most 40° C. introduced from the bottom of an ethylene oxide stripping column 8 through a line 9 in a counter current and then the ethylene oxide is absorbed. The absorption solution is then supplied from the bottom of the column 7 through a line 10 to the ethylene oxide stripping column 8, where the ethylene oxide is stripped by heating and sent from the top of the column 8 to a purification step.

The bottom liquid substantially removed with the ethylene oxide is recycled through the line 9 to the ethylene oxide absorption column 7 as the absorption solution. While on the other hand, pure oxygen is fed through a line 12 to the ethylene oxide absorption column 7 and mixed with a unabsorbed gas (a mixture of unreacted ethylene, oxygen, gaseous carbon dioxide, dilution gas, etc.) in a manner described latter, a part of which is recycled through a line 12 to the reactor 5 and the remaining part of which is introduced to a gaseous carbon dioxide absorption column 13, where it is contacted in a counter current manner with an alkaline absorption solution, for example, an aqueous solution of potassium carbonate supplied from a gaseous carbon dioxide stripping column 14 for the separation of gaseous carbon dioxide by absorption. The absorption solution is sent to the gaseous carbon dioxide stripping column 14, where the carbon dioxide is stripped and removed from the top of the column 14. The unabsorbed gas is sent from the top of the gaseous carbon dioxide absorption column 13 through a line 15 to the line 3, mixed with newly supplied fresh ethylene, dilution gas and the like and then recycled to the reactor 5.

Figure 2:
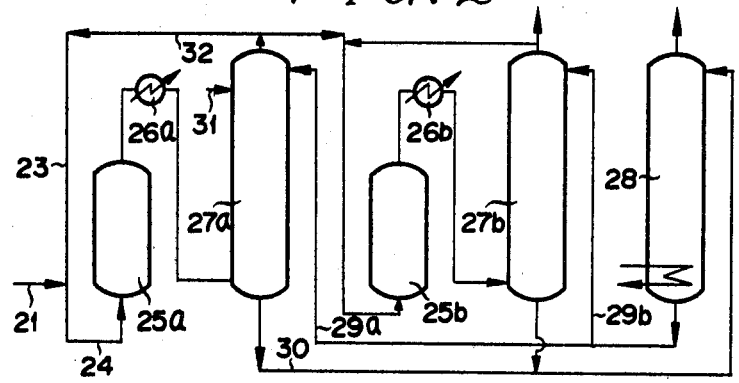
FIG. 2 is a flow sheet showing one example, wherein the method for mixing according to the present invention is applied to a process for producing ethylene oxide by oxidation reaction using air.

FIG. 2 is a flow sheet showing the principle of an oxidation process using air, in which ethylene supplied from a line 21 is mixed with a gaseous mixture comprising ethylene and air recycled from a line 23, sent into a first reactor 25a through a line 24 and then catalytically oxidized in a gas phase. The gaseous reaction products containing ethylene oxide and leaving the first reactor 25a are cooled to a predetermined temperature in a cooler 26a, introduced into the lower portion of a first absorption column 27a at a pressure of 2–40 kg/cm² and contacted, in a counter current manner, with water at a temperature of at most 40° C. introduced from the top of the column 27a or with an absorption solution containing an aqueous solution of ethylene glycol at a temperature of at most 40° C. introduced from the bottom of a stripping column 28 through a line 29a, whereby the ethylene oxide is absorbed. Air is supplied from a line 31 to the first absorption column 27a and mixed with a gas not absorbed (a mixture of unreacted ethylene, nitrogen, gaseous carbon dioxide and the like). A portion of the gas mixture is sent by way of a line 32 to the line 23, mixed with fresh ethylene or the like newly supplied, and then recycled to the first reactor 25a. The remaining portion of the gas mixture is supplied to a second reactor 25b and subjected to catalytic gas phase oxidation. The gaseous reaction products containing ethylene oxide and leaving the second reactor 25b are cooled to a predetermined temperature in a cooler 26b, thereafter, sent to a second absorption column 27b and then contacted, in a counter current manner, with water or an aqueous solution of ethylene glycol supplied from a line 29b in the same way as in the first absorption column 27a, whereby the ethylene oxide is removed by absorption. A portion of an unabsorbed gas recycled to the second reactor 25b and the rest is sent either to a purging step (not shown) or to a third reactor (not shown) for a further catalytic gas phase oxidation. The bottom solution in the first and the second absorption columns 27a and 27b are sent from a line 30 to a stripping column 28, where the ethylene oxide is stripped by heating and sent from the top of the column 28 to a purification step.

Figure 4:
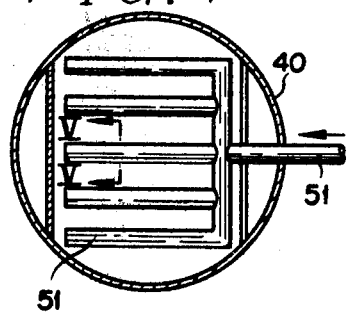
FIG. 4 is a cross sectional view taken along line IV—IV in FIG. 3.
Figure 3:
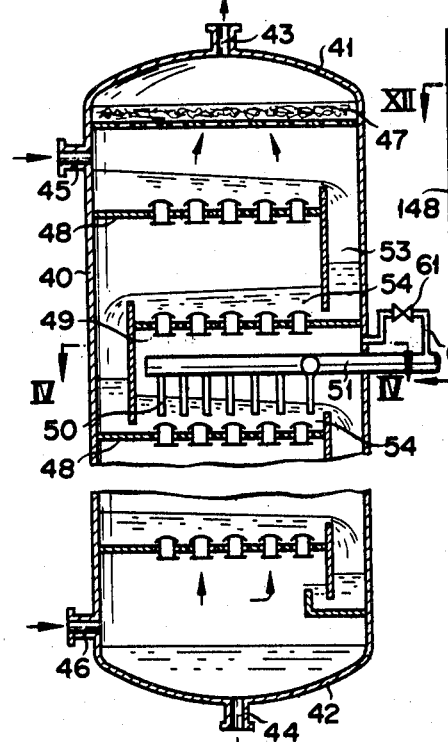
FIG. 3 is a vertical cross sectional view showing a preferred embodiment of the mixing apparatus according to the present invention.
Figure 5:
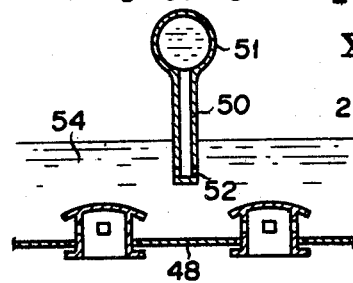
FIG. 5 is an enlarged cross sectional view of a part taken along line V—V in FIG. 4.

FIGS. 3–5 show a preferred embodiment of the gas mixing apparatus according to the present invention, wherein an ethylene oxide absorption column is used. In this mixing apparatus, a cylindrical main body 40 is tightly closed with end cap plates 41 and 42 secured to its upper end and lower end respectively, the upper end cap plate 41 having an exit 43 for the mixture of ethylene and oxygen, the lower end cap plate 42 having an exit 44 for an absorption solution and the main body 40 having an inlet 45 for absorption solution at it upper portion and an inlet 46 for oxidation reaction products at its lower portion. The main body 40 has provided therein, a demister 47 at its uppermost portion and a plurality of tray 48 (for example, ballast trays in 30-stage) therebelow. Between specific adjacent trays 48, is formed a gas mixing chamber 49 to which is inserted and mounted an oxygen feed pipe 51 having a plurality of branched tubes 50. One or more orifices 52 are provided to the bottom of each branched tubes 50.

An aqueous solution of ethylene glycol at 10% by weight concentration used as an absorption solution in the ethylene oxide absorption column 7 (gas mixing apparatus) is supplied from the inlet 45 to the uppermost tray 48. Then it falls through a downcomer 53 and gradually passes through the lower trays 48 successively to arrive at the bottom while contacting the reaction products of ethylene oxidation, and sent by way of the exit 44 to the ethylene oxide stripping column.

While on the other hand, pure oxygen is introduced together with a slight amount of nitrogen from a conduit 50 and mixed with the oxidation products blown out into an absorption solution 54 resident on the tray 48. The gas thus mixed is passed through the demister 47 and then discharged through the exit 43. In FIG. 3, a reference numeral 60 represents pressure-levelling line and a reference numeral 61 represents a value. The valve 61 is normally closed but rendered open by the absorption solution sucked into the pipe due to the negative pressure therein caused by the interruption of the oxygen source upon generation of an abnormality on the side of the pipe 51. As a result, the gas in the gas mixing chamber flows from the pressure-levelling line 60 to recover pressure balance and resume the liquid level.

Figure 7:
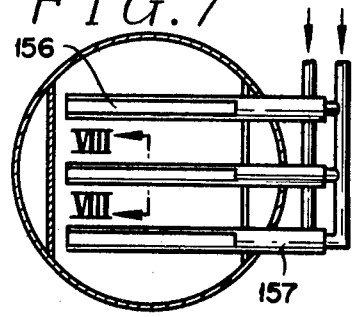
FIG. 7 is a cross sectional view taken along line VII—VII in FIG. 6.
Figure 6:
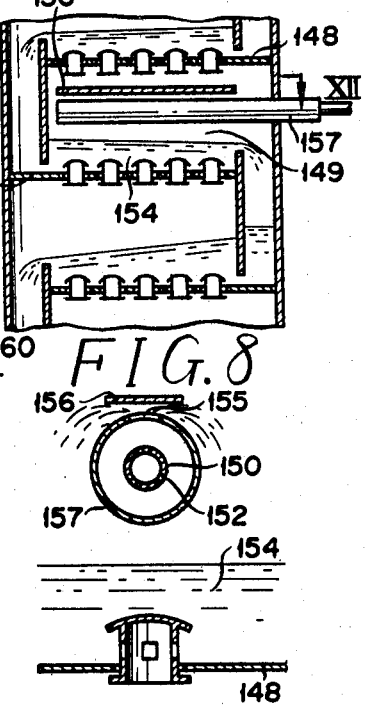
FIG. 6 is a vertical cross sectional view of a part in another preferred embodiment of the mixing apparatus according to the present invention.
Figure 8:
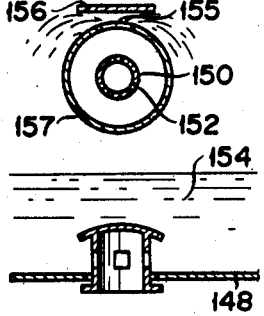
FIG. 8 is an enlarged cross sectional view of a part taken along line VIII—VIII in FIG. 7.

FIGS. 6-8 show another embodiment of the present invention which comprises, in a gas mixing chamber 149 defined between adjacent trays 148, an oxygen feed means comprising a double pipe composed of an inner pipe 150 having a plurality of orifices 152 and an outer pipe 157 having an opening 155 at its upper portion and a baffle plate 156 disposed thereabove substantially horizontally above the liquid surface of an absorption solution 154 on a tray 148 so as not to result flooding. An oxygen-containing gas, for example, pure oxygen is introduced from the inner pipe 150 and purified water is introduced from the outer pipe 157. The oxygen is caused to pass from the inside of the orifices 152 provided in the inner pipe 150 as gas bubbles through the layer of purified water and flows out together with water through a gap between the baffle plate 156 keeping the absorption solution from entering the outer pipe 157 and the opening 155 of the outer pipe 157 and then mixed with gaseous oxidation products.

Figure 9:
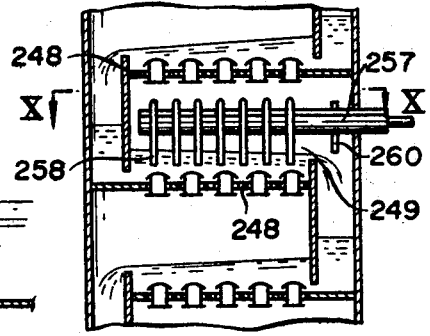
FIG. 9 is a vertical cross sectional view of a part in a further embodiment of the mixing apparatus according to the present invention.

FIGS. 9-11 show another embodiment of the present invention, wherein a double pipe composed of an inner pipe 250 having a plurality or orifices 252 and an outer pipe 257 having at its upper portion a plurality of branched pipes 258 each with one or more orifices 259 at the top is inserted in a gas mixing chamber 249 defined between adjacent trays 248. An oxygen-containing gas, for example, pure oxygen is introduced through the inner pipe 250 and purified water is introduced through the outer pipe 257. The oxygen is introduced from the inside of the orifices 252 disposed in the inner pipes 250 as gas bubbles through the layer of purified water and then blown out together with the purified water from the orifices 259 of the branched pipes 258, and then mixed with the gaseous oxidation products. In FIGS. 9-11, a reference numeral 260 represents a pressure levelling line.

In the present invention, introduction means for molecular oxygen-containing gas of the above first to third types (FIGS. 3-11) may be provided on any of the trays in a gas mixing apparatus utilizing an absorption column but it is desirably provided on the tray between (and including) the uppermost to the fifth tray from the uppermost tray where the concentration of the gas to be absorbed is low.

FIG. 12 shows another embodiment of the present invention which is constituted quite in same manner as in FIGS. 3-5 excepting that an oxygen introducing pipe 351 having a plurality of branched pipes 350 each with an orifice at its end is provided between the uppermost tray 348 and a demister 347.

FIG. 13 shows another embodiment of the present invention which is constituted quite in same manner as in FIGS. 6-8 excepting that a double pipe composed of an inner pipe 450 having a plurality of orifices and an outer pipe 457 having an opening at its upper portion and a buffle plate 450 thereabove as shown in FIG. 8 is provided as an oxygen feed means between the uppermost trays 448 and a demister 447.

FIG. 14 shows another embodiment of the present invention which is constituted quite in the same manner as in FIGS. 9-11 excepting that a double pipe composed of an inner pipe 550 having a plurality of orifices and an outer pipe 557 having a bundle of branched tubes 558 at its upper portion each with an orifice at its end as shown in FIG. 11 is provided as an oxygen feed means between the uppermost tray 548 and a demister 547.

The diameter and the number of the orifices formed in the oxygen-containing gas introduction pipe in the present invention are determined depending on the pressure loss allowable in the production apparatus and they are, desirably, designed so as to give 0.1–3 kg/cm$^2$ of pressure loss in a usual condition.

What is claimed is:

1. An apparatus for mixing a hydrocarbon-containing gas flow with a molecular oxygen-containing gas flow comprising
    a cylindrical main body;
    an exit and an inlet for the hydrocarbon-containing gas flow provided respectively to the upper and the lower portions of said cylindrical main body;
    an inlet and an exit for an aqueous medium provided respectively to the upper and the lower portions of said main body;
    at least one aqueous medium residence means provided on the inlet side of the hdyrocarbon-containing gas flow in the main body and allowing said gas flow to pass therethrough in connection with said aqueous medium;
    at least one shielding means for flame propagation provided on the discharge side of said hydrocarbon-containing gas flow in the main body and allowing said gas flow to pass therethrough; and
    an introduction means for the molecular oxygen-containing gas flow provided in a gas mixing chamber formed in a space defined by said residence means and said shielding means connected to a plurality of bundles of pipes each having at least one orifice at the end, the orifices of said bundles of pipes are immersed in the layer of the aqueous medium on the aqueous medium residence means.

2. An apparatus as defined in claim 1, wherein the aqueous medium is water.

3. An apparatus as defined in claim 1 wherein the aqueous medium residence means is trays.

4. An apparatus as defined in claim 1, wherein the aqueous medium residence means is packings.

5. An apparatus as defined in claim 1, wherein the shielding means for flame propagation is the aqueous medium residence means.

6. An apparatus as defined in claim 1, wherein the shielding means for flame propagation is a demister.

7. An apparatus as defined in claim 1, wherein the introduction means for the molecular oxygen-containing gas is provided, at the lowest, to a fifth tray from the top.

8. An apparatus as defined in claim 1, wherein the hydrocarbon-containing gas is reaction products of catalytic gas phase oxidation of hydrocarbon still containing unreacted hydrocarbons.

9. An apparatus as defined in claim 1, wherein the hydrocarbon is ethylene.

10. An apparatus as defined in claim 9, wherein the aqueous medium is an aqueous solution of ethylene glycol 0.1–30% by weight in concentration.

11. An apparatus for mixing a hydrocarbon-containing gas flow with a molecular oxygen-containing gas flow comprising a cylindrical main body;

an exit and an inlet for the hydrocarbon-containing gas flow provided respectively to the upper and the lower portions of said cylindrical main body;

an inlet and an exit for an aqueous medium provided respectively to the upper and the lower portions of said main body;

at least one aqueous medium residence means provided on the inlet side of the hydrocarbon-containing gas flow in the main body and allowing said gas flow to pass therethrough in connection with said aqueous medium;

at least one shielding means for flame propagation provided on the discharge side of said hydrocarbon-containing gas flow in the main body and allowing said gas flow to pass therethrough; and an introduction means for the molecular oxygen-containing gas flow provided in a gas mixing chamber formed in a space defined by said residence means and said shielding means comprising a double pipe composed of an inner pipe for flowing the molecular oxygen-containing gas and having a plurality of orifices and an outer pipe for flowing water and having an opening at its upper portion, and said introduction means is provided in the gas phase in said gas mixing chamber.

12. An apparatus for mixing a hydrocarbon-containing gas flow with a molecular oxygen-containing gas flow comprising a cylindrical main body;

an exit and an inlet for the hydrocarbon-containing gas flow provided respectively to the upper and the lower portions of said cylindrical main body;

an inlet and an exit for an aqueous medium provided respectively to the upper and the lower portions of said main body;

at least one aqueous medium residence means provided on the inlet side of the hydrocarbon-containing gas flow in the main body and allowing said gas flow to pass therethrough in connection with said aqueous medium;

at least one shielding means for flame propagation provided on the discharge side of said hydrocarbon-containing gas flow in the main body and allowing said gas flow to pass therethrough; and an introduction means for the molecular oxygen-containing gas flow provided in an gas mixing chamber formed in a space defined by said residence means and said shielding means comprising a double pipe composed of an inner pipe for flowing the molecular oxygen-containing gas flow having a plurality of orifices and an outer pipe for flowing water flow having a plurality of orifices and an outer pipe for flowing water flow having a plurality bundle of branched pipes at its upper portion each with at least one orifice, and the orifices at the ends of said branched pipes are adapted to be immersed in the layer of the aqueous medium on the aqueous residence means.

* * * * *